(12) United States Patent
Wang et al.

(10) Patent No.: US 7,418,866 B2
(45) Date of Patent: Sep. 2, 2008

(54) METHOD AND APPARATUS FOR EVALUATION OF STANDING TIMBER

(75) Inventors: Xiping Wang, Verona, WI (US); Nigel Sharplin, Waikuku Beach (NZ); Peter Carter, Papatoetoe (NZ); Robert J. Ross, Madison, WI (US)

(73) Assignees: Regents of the University of Minnesota, Minneapolis, MN (US); The United States of America as represented by the Secretary of Agriculture, Washington, DC (US); Fibre-gen Instruments Limited, Auckland (NZ)

( * ) Notice: Subject to any disclaimer, the term of this patent is extended or adjusted under 35 U.S.C. 154(b) by 211 days.

(21) Appl. No.: 11/038,968

(22) Filed: Jan. 20, 2005

(65) Prior Publication Data

US 2005/0160819 A1 Jul. 28, 2005

Related U.S. Application Data

(60) Provisional application No. 60/538,376, filed on Jan. 22, 2004.

(51) Int. Cl.
   *G01N 29/07* (2006.01)
(52) U.S. Cl. .............................. 73/597; 73/598; 73/644
(58) Field of Classification Search ................. 73/597, 73/644, 598, 632, 579
   See application file for complete search history.

(56) References Cited

U.S. PATENT DOCUMENTS

| | | | |
|---|---|---|---|
| 3,066,525 A * | 12/1962 | Harris | ......................... 73/644 |
| 4,838,085 A | 6/1989 | Pellerin et al. | |
| 5,024,091 A | 6/1991 | Pellerin et al. | |
| 5,278,423 A * | 1/1994 | Wangler et al. | .......... 250/559.4 |
| 5,307,679 A | 5/1994 | Ross | |
| 5,396,799 A | 3/1995 | Ross et al. | |
| 6,029,522 A | 2/2000 | Schafer et al. | |
| 6,092,418 A | 7/2000 | Schafer et al. | |
| 6,276,209 B1 * | 8/2001 | Schafer et al. | ................. 73/597 |
| 6,295,907 B1 | 10/2001 | Schafer et al. | |
| 6,305,224 B1 * | 10/2001 | Stanish et al. | .................. 73/597 |
| 6,308,571 B1 * | 10/2001 | Stanish et al. | .................. 73/597 |
| 6,457,363 B1 | 10/2002 | Schafer | |
| 6,467,352 B2 | 10/2002 | Schafer et al. | |
| 6,472,981 B1 * | 10/2002 | Fuge et al. | ................ 340/539.1 |
| 6,598,477 B2 * | 7/2003 | Floyd | ............................ 73/597 |
| 6,784,672 B2 * | 8/2004 | Steele et al. | .................. 324/663 |
| 6,871,545 B2 * | 3/2005 | Huang | ............................ 73/597 |
| 6,941,816 B2 * | 9/2005 | Kurtz et al. | .................... 73/756 |
| 7,017,413 B2 * | 3/2006 | Floyd et al. | .................... 73/597 |
| 2002/0112542 A1 | 8/2002 | Walker | |
| 2004/0181154 A1 * | 9/2004 | Peterson et al. | ............. 600/459 |
| 2005/0138995 A1 * | 6/2005 | Wilhelm | ........................ 73/104 |

FOREIGN PATENT DOCUMENTS

| EP | 1 008 848 A2 | 11/1999 |
|---|---|---|
| TW | 237687 B1 * | 4/2004 |
| WO | WO 02/060662 A2 | 8/2002 |

* cited by examiner

*Primary Examiner*—Hezron E. Williams
*Assistant Examiner*—Jacques M. Saint-Surin
(74) *Attorney, Agent, or Firm*—Boyle Fredrickson S.C.

(57) ABSTRACT

A method and apparatus for measuring the quality of live, standing timber employs deep-set spike probes angled to create a longitudinal compression wave. Alignment tools and isolation of the probes provide an improved signal, automated detection of probe separation and amplitude-independent pulse discrimination process ensure higher reliability and repeatability of the measurements, and wireless operation provides operational efficiencies.

28 Claims, 4 Drawing Sheets

METHOD AND APPARATUS FOR EVALUATION OF STANDING TIMBER

CROSS-REFERENCE TO RELATED APPLICATIONS

This application claims the benefit of U.S. provisional application No. 60/538,376 filed Jan. 22, 2004, hereby incorporated by reference.

STATEMENT REGARDING FEDERALLY SPONSORED RESEARCH OR DEVELOPMENT

This invention was made with United States government support under 01-JV-111111132-118 and 02-JV-111111132-118 awarded by the U.S. Department of Agriculture. The government has certain rights in this invention.

BACKGROUND OF THE INVENTION

This invention relates generally to an apparatus and method for acoustically testing wood properties and suitable for live, standing trees.

Currently, it is difficult to nondestructively assess wood quality in standing trees. In order to evaluate wood quality, a forester must take samples of the wood and send them to a laboratory for analysis, or fell the tree first and make a visual inspection of the external characteristics of the logs cut from the tree. Often a complete assessment of wood quality cannot be made until the timber is in the milling process. By this time, considerable resources have been spent locating and transporting the timber. Discovering that the timber is not of usable quality is a waste of these limited resources. Furthermore, otherwise useful trees are unnecessarily removed from the forest.

The measurement of sound speed through wood is a well-known method for evaluating logs and timber. Sound speed is generally related to the modulus of elasticity of the wood and may indicate additional properties related to wood strength and quality. Typically in such techniques, a resonance-based approach may be used or an acoustic signal is introduced into one end of a log or at the end or surface of exposed timber, and its time of transit to the other end or separate point is recorded. Sound speed is derived simply by dividing the transit time by the length of the sound path through the log or timber.

PCT patent application WO 02/29398 describes a variation on this technique for use with standing trees. Following the method of this patent application, shallow spikes held in separation by a rigid bar are used to introduce sound waves into the cambium of the tree at a first location and extract the sound waves at a second location a predetermined distance away from the first location. The time between a tapping of the first spike and a receipt of the sound wave at the second spike displaced by the known length of the rigid bar provides a measure of sound speed that may be used to deduce modulus of elasticity. One drawback to this system is possible acoustic contamination from sound passing not through the wood, but directly between the probes through the connecting bar.

New Zealand patent application No. 533153, filed May 26, 2004 by inventor Chin-Lin Huang, entitled: "System and Method for Measuring Stiffness in Standing Trees" and claiming priority from U.S. patent application Ser. No. 10/600,933 filed Jun. 20, 2003, describes a similar system, but in which the probes are separate, to be freely located on the sides of the tree held by spikes engaging the cambium wood. Each probe communicates by means of electrical cables to a measuring unit. Because the probes are connected only by flexible cables to the measuring unit, the sound detected by the receiving probe is not contaminated with sound through a connecting bar.

The use of two separate probes, unconnected by a bar, reduces the weight and bulk of the system, simplifying its use by a single operator in the field. Yet because the probes are no longer held in rigid separation, their separation distance, which must be known for accurate sound speed measurement, will vary. This variation can be accommodated by the additional step of having the operator measure the separation between the probes, for example, using graduations on the connecting cables as a ruler as proposed in the 533153 patent, but this added measurement introduces possible operator error and decreases the convenience and speed with which the system may be used.

When separate probes are used, they can be misaligned when installed on the tree, significantly decreasing the strength of the received acoustic signal, and hence accuracy of the measurement. The electrical connections between the probes and measuring unit, no longer routed along the separating bar, may become tangled and damaged.

BRIEF SUMMARY OF THE INVENTION

The present invention provides the benefits of separate probes without many of the disadvantages of separate probes by employing a series of wireless links between the probes (and a measuring unit), each link tailored to a particular task. The result is a probe system that is easy to install and move and yet which provides high accuracy.

In one embodiment, an ultrasonic pulse is used to automatically measure the separation between the probes. A laser checks alignment between the probes, while a high speed infrared pulse communicates the start time of the pulse from one probe to the other. Finally, a radio link is used to communicate data to a separate measurement unit.

Each of these links connects the units without direct contact, eliminating any path of acoustic contamination between the probes and avoiding the need for cumbersome and damage-prone cables and electrical connectors.

The present inventors have developed a number of other innovations that improve sound speed measurements applied to standing trees. First, spikes that may pierce the bark and cambium and extend into the sapwood are used to direct acoustic energy into a tree across a larger proportion of the cross-section of the tree trunk. Second, a sophisticated processing of the received acoustic pulse is used to provide an arrival time measurement that is less sensitive to signal amplitude variations than is a simple voltage threshold detection technique used in the prior art. In addition to sound speed measured in standing trees, several other predictor parameters have been incorporated into more sophisticated prediction models that are more reliable and accurate than is a simple sound-speed-only-based model. These additional parameters may include breast height diameter (DBH) of a tree, the age of a tree, tree species and wood temperature individually or in combination. DBH and wood temperature are the most significant parameters in addition to sound speed. Tree age and tree species are preferably added into the model if they are available at the time of assessing trees. In one embodiment, a tree-grading program then assigns quality levels to individual trees based on these measurements and derives plot, stand, or forest-level summary outputs.

Specifically, then the present invention may provide a first and second acoustic probe attachable to a tree at different heights to engage the wood of the trunk and to provide an acoustic transmission signal and an acoustic reception signal indicating, respectively, a time of initiation of an acoustic wave into the wood by the first acoustic probe and a time of receipt of the acoustic wave through the wood at the second probe. The probes are adapted to transmit a longitudinal compression wave through the bulk wood (both sapwood and heartwood) in the tree from the first probe to the second probe and to detect the longitudinal compression wave passing through the tree at the second probe. Analysis circuitry communicating with the first and second acoustic probes may receive an acoustic transmission signal (start signal) and an acoustic reception signal (stop signal) to provide a speed of sound measurement of the acoustic wave through the wood. A wireless communication link may transmit at least one of the acoustic stop signal and acoustic start signal to the analysis circuitry, the wireless communication link providing a speed of transmission substantially greater than a speed of propagation of the acoustic wave.

Thus, in at least one embodiment, the invention eliminates the possibility of conduction of the excitation signal through the support structure to the receiving transducer such as may introduce error into the timing measurements and eliminates the need for wires or other physical connections between the spikes, so improving greatly the ease with which the device may be used in the field.

The wireless communication link may be an infrared diode transmitting the acoustic start signal from the first probe to the analysis circuitry.

Thus it is an object of at least one embodiment of the invention to provide a wireless communication of the start pulse arrival time that can be transmitted reliably, at low cost, and with essentially no delay.

The analysis circuitry may be attached to the second acoustic probe.

Thus it is another object of at least one embodiment of the invention to ensure consistent and reliable communication between the transmitting probe and this circuitry. It is another object of at least one embodiment of the invention to eliminate the need for two wireless links in this critical measurement path.

The invention may include a data logging unit storing speed of sound measurements and a second wireless communication link transmitting speed of sound measurement data from the analysis circuitry to the data logging unit.

Thus it is another object of at least one embodiment of the invention to provide a convenient means of analyzing and transporting collected data free from the collection hardware.

The invention may include a range-detecting sensor communicating between the first and second acoustic probes to provide a separation measurement signal indicating a separation between the first and second acoustic probes, and the analysis circuitry may use the separate measurement signal in determining the speed of sound measurement.

Thus it is another object of one embodiment to reduce the error in length measurement between the spikes when a separating bar is not employed.

The invention may further include an alignment sensor communicating between the first and second acoustic probes to indicate whether the spike of the first and second acoustic probes lies within a single common plane.

Thus, it is another object of at least one embodiment of the invention to lessen signal loss and signal-to-noise induced error caused by off-axis or out-of-alignment probe insertion in a field environment.

The second probe may include a transducer for generating an electrical signal measuring the acoustic wave received at the second probe, and the invention may provide a pulse discrimination circuitry receiving the electrical signal and generating a pulse stop signal using an amplitude independent detection process.

Thus, it is another object of one embodiment to eliminate variations in sound speed measurement caused by amplitude variations that may occur when testing trees in a field situation.

The first and second probes may include spikes adapted to be driven through bark and cambium of the tree to engage the sapwood beneath the cambium.

Thus, it is an object of this embodiment to provide a method for introducing longitudinal compression waves deep into the tree without access to exposed wood or log ends.

The pulse start signal is provided by an electrical switch actuatable by the striking of the first acoustic probe with a mallet.

One object of at least one embodiment of the invention may therefore provide a simple means for detecting the start of the acoustic signal.

One embodiment of the invention provides a method for predicting the modulus of elasticity (MOE) (a measure of wood stiffness) and other wood and fiber properties (such as strength, density, fiber length, microfibril angle, but not limited to these) through pre-established multivariate prediction models. The predictor parameters may include sound speed and DBH of a tree, as well as tree age and species if they are available.

Another embodiment of the invention provides a procedure for generating statistic outputs for specific plot, stand, or forest evaluated. The statistic outputs include mean, standard deviation, 95 percent confidence level for various tree measures such as sound speed, DBH, and predicted wood and fiber properties.

The invention may include a software program to assign quality levels to individual trees and specific plot, stand, or forest according to pre-determined grading criteria. The grading criteria may be adjusted by users based on their particular needs and the types of wood and fiber products that they wish to produce from the trees.

These particular objects and advantages may apply to only some embodiments falling within the claims and thus do not define the scope of the invention.

BRIEF DESCRIPTION OF THE DRAWINGS

FIG. 3 is a block diagram showing the components of the present invention in one embodiment such as may communicate with a personal digital assistant or the like;

DETAILED DESCRIPTION OF THE PREFERRED EMBODIMENT

Figures 1, 2:
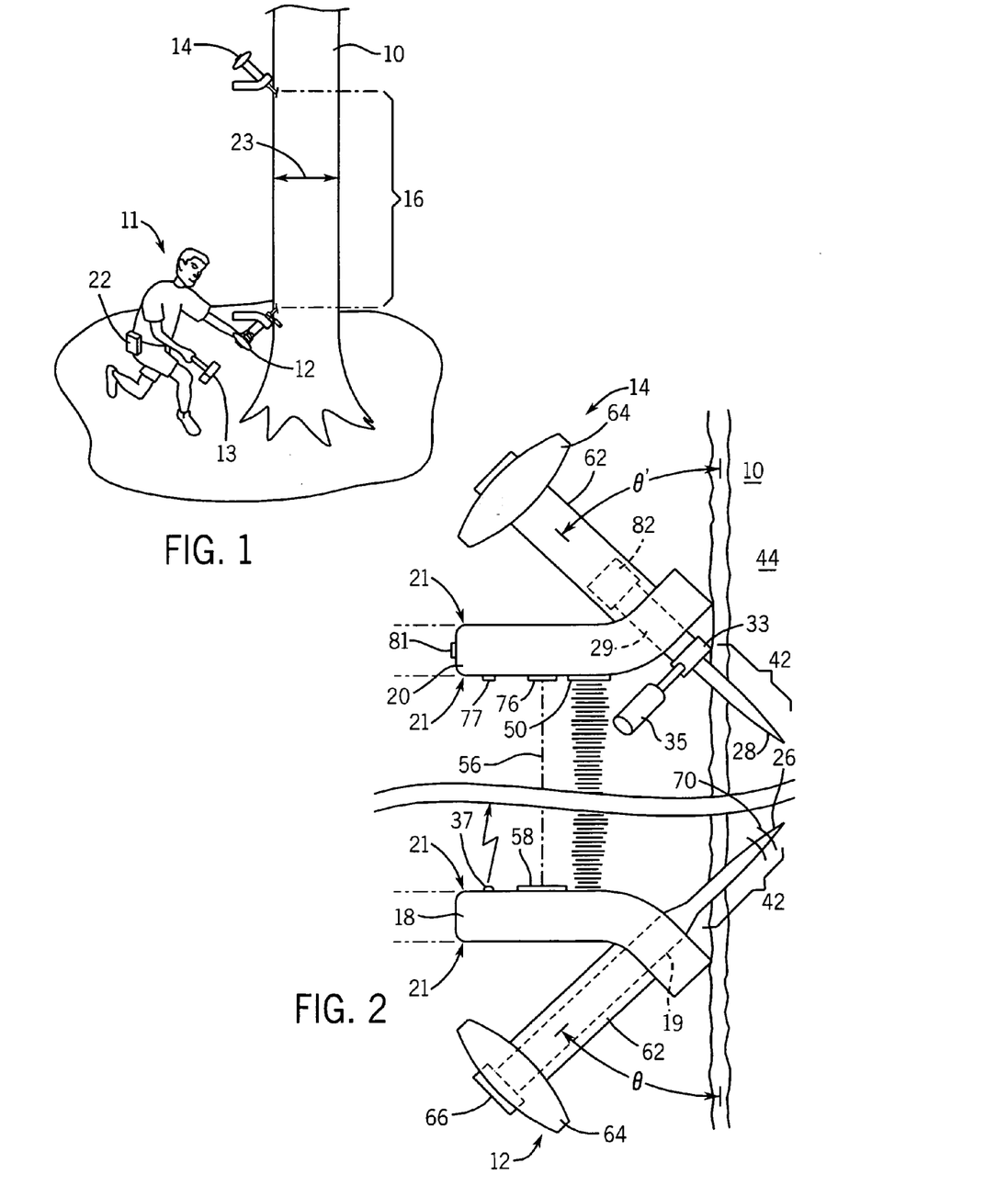
FIG. 1 is a perspective view of a standing tree with spike probes of the present invention being inserted through its bark by an operator.
FIG. 2 is a fragmentary elevational cross-section of the tree of FIG. 1 showing positioning of the spike probes therein.

Referring to FIG. 1 generally, the present invention may be used to measure the wood quality of a live, standing tree 10 by an individual forester 11 who may carry the components of the present invention easily from tree to tree.

At each tree 10 to be measured, the forester 11 hammers two spikes into the tree using a hammer 13. As shown in FIG. 1, the first spike associated with transmitting acoustic probe 12, is angled upward into the tree 10 near the ground and a second spike, associated with receiving acoustic probe 14, is positioned at about eye level and angled downward into the tree 10 toward the transmitting acoustic probe 12. The distance 16 between the transmitting acoustic probe 12 and the receiving acoustic probe 14 is not critical and may vary between one foot and six feet with a distance of about four feet preferred because it is consistent with the average height that a forester can reach. Longer separations may also be possible. The transmitting acoustic probe 12 may alternatively be above the receiving acoustic probe 14 provided they are generally in a vertical line with respect to one another along the grain of the wood.

After installation of the transmitting acoustic probe 12 and the receiving acoustic probe 14, the forester 11 may make a measurement of the breast height diameter (DBH) 23 of the tree as may optionally be used in the calculation of wood quality to be described below. The forester 11 may carry a personal digital assistant (PDA) 22 providing for convenient interface with the electronics of the invention as will be described.

Referring now to FIG. 2, the spike 26 of the transmitting acoustic probe 12 may be guided during insertion into the tree 10 by a housing 18 having an internal angled channel 19 providing the proper angulation of the transmitting acoustic probe 12 when a reference surface 21 of the housing 18 is approximately level. This angle $\theta$ is preferably about 45 degrees and results in a sharpened tip of the spike 26 of transmitting acoustic probe 12 being angled toward a tip of spike 28 of the receiving acoustic probe 14. The spike 28 is held positioned by a second housing 20 of similar construction to housing 18 holding the spike 28 of the receiving acoustic probe 14 at a mirror image angle $\theta'$.

Figure 8:
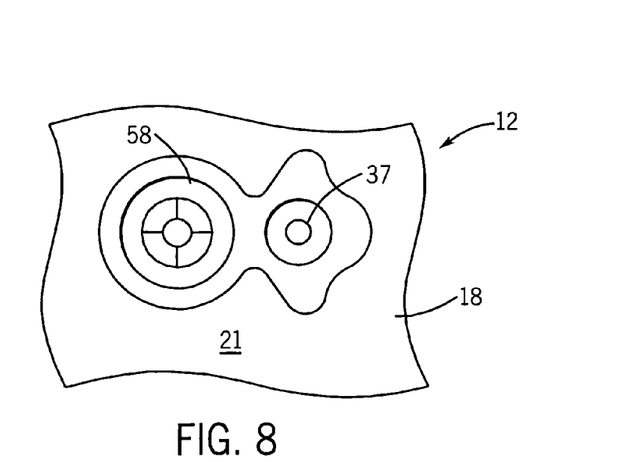
FIG. 8 is a top plan view of a laser target and infrared transmitter used on the transmitting probe.

The angle of the spike 28 may also be guided by the use of a laser beam 56 (to be described below) emitted from a laser 76 at a 45 degree angle to spike 28 and perpendicular to reference surfaces 21, and directed downward at a target 58 (shown in FIG. 8) on the housing 18 of the receiving acoustic probe 14. Both the laser 76 and the target 58 are at a same distance from the tips of spikes 26 and 28 on the respective housings 18 and 20.

Figure 3:
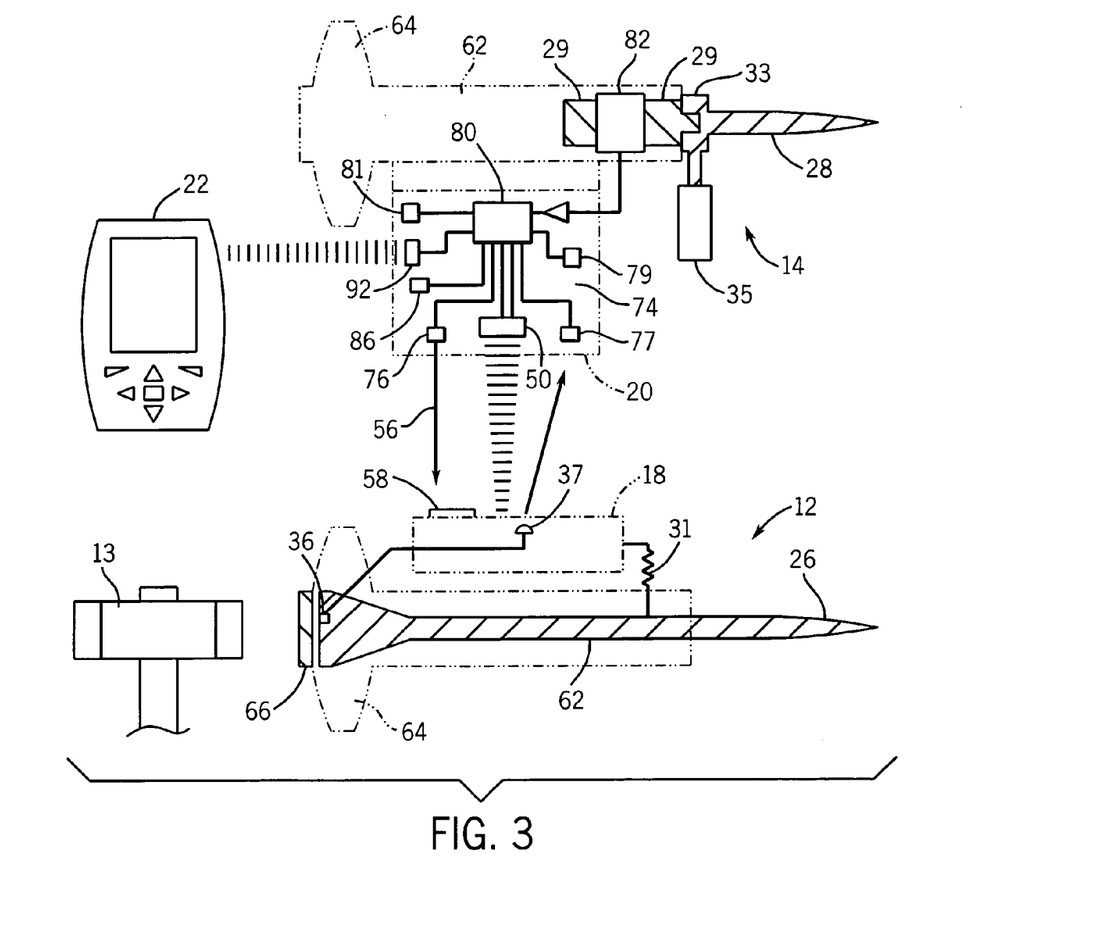

Referring to FIGS. 2 and 3, the channel 19 is connected to the spike 26 through a spring coupling 31 to allow movement of the spike 26 without the need to accelerate the housing 18, protecting the circuitry within the housing 18 (to be described) and providing a faster acceleration of the spike 26 upon impact by the hammer 13.

In contrast, the spike 28 of the probe 14 is removable and may be installed by striking a collar 33 on the outer end of the spike 28 with the hammer 13. A handle 35 attached to the collar 33 and extending radially from the axis of the spike 28 may be used to hold and guide the spike 28 during this process. In this way, the circuitry (to be further described) in the housing 20 and other components of the acoustic probe 14 are wholly protected from the shock of installing the spike 28 into sapwood (as will also be described).

When the spike 28 is installed, an upper shaft 29 is fit to the collar 33 by means of a mating pin and socket to attach the probe 14 to the spike 28 held by gravity and/or a loose press fit. Whereas such a separation in the length of the spike can be detrimental in the spike 26 of probe 12, the present inventors have determined that this separation is readily accommodated in the spike 28 of the receiving probe 14. Once the spike 28 is assembled to the upper shaft 29, the handle 35 may be used to further adjust the alignment of the spike 28 as will be described.

The reference surfaces 21 generally guide the installation of the probes 12 and probe 14 by the forester endeavoring to approximately place these reference surfaces 21 in a horizontal or other reference plane. Final alignment is accomplished with the laser 76.

The spikes 26 and 28 are preferably driven into the tree to a depth of from ten to twenty millimeters to allow a portion 42 of the spikes 26 and 28 to acoustically couple with sapwood 44 beneath both the bark 24 and cambium 25 being generally the older wood outside of a core layer of the tree as is generally understood in the art.

The spikes 26 and 28 may be constructed of stainless steel, titanium, or other suitable materials to readily pierce the sapwood 44 and the bark 24 and cambium 25 and to provide a well characterized sound wave and to resist removal bending forces as will be discussed below. Generally, the portion 42 of the spikes 26 and 28 within the sapwood 44 tapers continuously from the tips outward as one passes through the bark 24 so as to provide compressive purchase against the wood fiber of the sapwood 44 that resists further insertion of the spikes 26 and 28 after a certain point and that eases removal of the transmitting acoustic probe 12 and receiving acoustic probe 14.

The spike 26 of transmitting acoustic probe 12 is surrounded at its distal end, by an elastomeric handle 60 having an outer grip portion 62 and a disk shield portion 64. The disk shield portion 64 protects a user's hand holding the outer grip portion 62 from errant hammer blows and provides a grip for withdrawing or extracting the transmitting acoustic probe 12 and receiving acoustic probe 14 after completion of the test.

The distal ends of the spike 26 holds a replaceable impact cap 66 constructed, for example, of a metal so as to resist damage by the hammer 13 and to control the characteristics of the acoustic signal that will be generated during the testing process by striking the transmitting acoustic probe 12 with the hammer 13 or other impact means. Impact cap 66 for transmitting acoustic probe 12 may include a mechanical contact switch 36 providing normally open contacts biased by a contained spring (not shown) that will contact during a hammer strike to produce an acoustic start signal as will be described. The switch 36 communicates with an infrared transmitter 37 exposed at the upper reference surface 21 of the housing 18 to communicate a pulse start signal to be described below. The housing 18 further holds batteries (not shown) for powering the infrared transmitter 37.

Referring still to FIGS. 2 and 3, a piezoelectric accelerometer 82 is attached to the upper shaft 29 of receiving acoustic probe 14 to sense axial vibrations conducted along the length of the spikes 26 and 28. The lower reference surface 21 of housing 20 exposes an ultrasonic range finder 50 that may transmit an ultrasonic beam 52 to a target, being the upper reference surface 21 of the probe 12, to thus determine the separation between housing 20 and 18. By the known geometry of the probes 12 and 14 and their respective spikes 26 and 28 with respect to the reference surfaces 21, the separation between the tips of spikes 26 and 28 can be determined. The lower reference surface also holds an infrared receiver 77 to detect the pulse start signal from the infrared transmitter 37.

Housing 20 also holds processing circuitry and a wireless communication device 92 on a contained circuit board 74 holding a microcontroller 80. The microcontroller 80 or the circuit board may incorporate a multiplexing A/D converter (not shown) which may receive the output of the accelerometer 82 and an ambient air temperature probe 86. Wood temperature may be deduced from ambient air temperature, or a separate temperature probe (not shown) can be incorporated into one or both spikes 26 and 28 to communicate with the A/D converter 84, or an average ambient temperature may be assumed from typical seasonal temperature data. Alternatively, a separate instrument may be used to measure wood temperature for selected trees during the measuring process. The microcontroller 80 may receive a digital output of the A to D converter as well as digital output from the range finder 50 and the infrared receiver 77 for the acoustic start signal from the impact cap 66 of the transmitting acoustic probe 12 as described above. The microcontroller 80 may also communicate with a wireless transmitter providing data exchange with a PDA 22 to read out or store data or provide programming input to the apparatus. The wireless transmitters and receivers of this type are well known in the art and include short radio links per the Bluetooth or IEEE wireless standards or alternatives known in the art.

Microcontroller 80 also communicates with a internal memory which contains an operating program, as will be described below, for processing the data collected by the apparatus and in handling other tasks that would be understood to those ordinarily skilled in the art. The circuit board 74 also provides an attachment to a battery pack (not shown) holding replaceable or chargeable batteries to provide electrical power to the described components. The microcontroller 80 may also communicate with a numeric display 81 exposed on a front vertical face of the housing 20. The microcontroller 80 may also communicate with an audio transducer providing audible signals to the forester 11.

Figure 4:
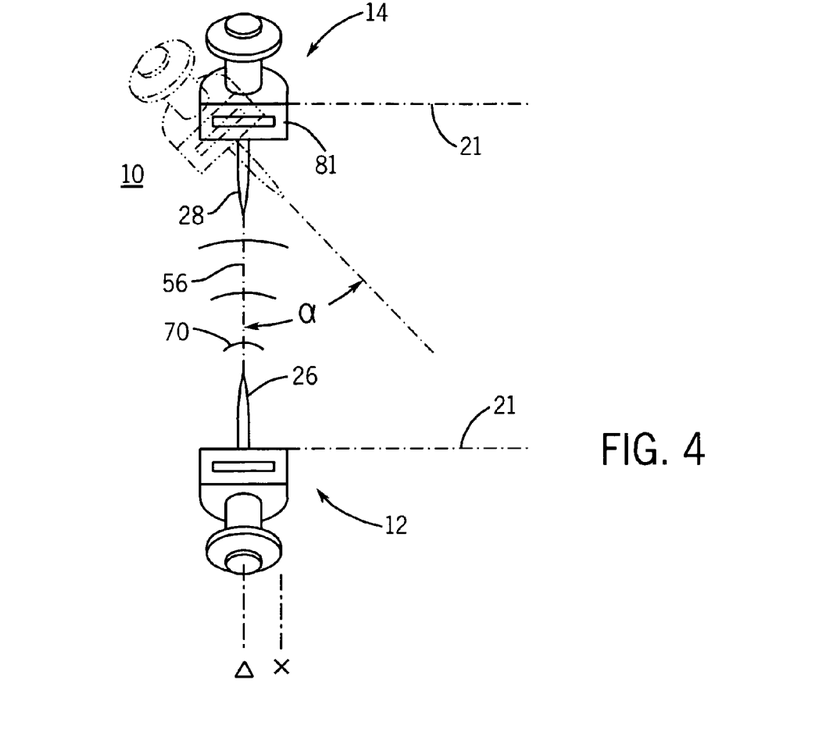
FIG. 4 is a front elevational view of the spike probes of FIG. 1 showing alignment of the probes in a single plane by an alignment guide and housing reference surface.

Referring now momentarily to FIGS. 2 and 4, the laser beam 56 allows for housing 18 and 20 to be aligned to ensure that acoustic energy in the form of longitudinal compression waves 70 are well coupled through the tree 10 between the transmitting acoustic probe 12 and receiving acoustic probe 14, and that automated length measurement between the spikes 26 and 28 is as accurate as possible. This alignment provides that angle α defining angular deviation between a plane perpendicular to the bark 24 and bisecting the spike 26 of the transmitting acoustic probe 12 and a plane perpendicular to the bark 24 and bisecting the spike 28 of the receiving acoustic probe 14 be close to zero. This alignment also provides that a separation of these planes Δx be close to zero. This alignment contributes to precision of automated length measurement and also to the strength of the signal passing between transmitting acoustic probe 12 and receiving acoustic probe 12 reducing signal-to-noise ratio of that signal such as may result in erroneous or irreproducible results.

Figure 6:
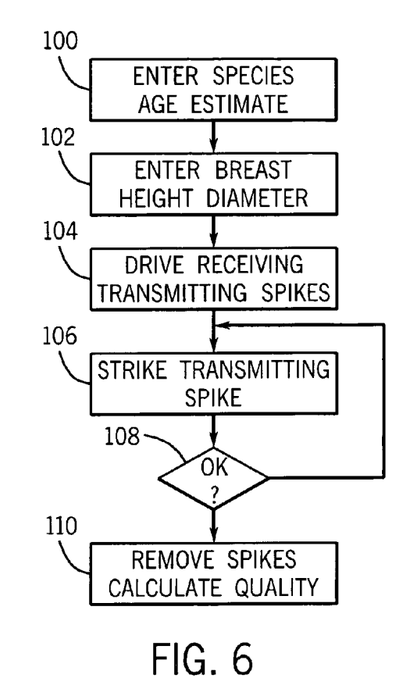
FIG. 6 is a flowchart showing the steps of the method of the present invention.

Referring now to FIG. 6, in a first step in the use of the present invention, the forester 11 enters the species and age estimate of the tree as indicated by process block 100 through the PDA 22.

At process block 102, the DBH 23 described above with respect to FIG. 1 is optionally measured (for example, with a tape measure or alternative measuring device) and entered through the PDA 22.

Per process block 104, the forester 11 then may drive the spikes 26 and 28 of the transmitting acoustic probe 12 and receiving acoustic probe 14 into the tree 10 as shown in FIG. 1, and after assembling the spike 28 to upper shaft 29, align the housings 18 and 20 per the discussion associated with FIG. 4. The transmitting acoustic probe 12 and receiving acoustic probe 14 are inserted into the tree 10 to a maximum depth such that tips of the spikes 26 and 28 are coupled to the sapwood.

After completion of driving the spikes 28 and 26 into position, the microcontroller 80 is armed either through a signal from the PDA 22 or a pushbutton (not shown) on one of the housings 18 and 20. At this time, the microcontroller, executing a stored program in memory 90, measures the separation distance of the housings 18 and 20, determines the separation of the receiving acoustic probe 14 and transmitter acoustic probe 12, and stores this number and displays it on the display 81 for confirmation.

At process block 106 of FIG. 6, and referring also to FIG. 3, the forester 11 may strike impact cap 66 of transmitting acoustic probe 12 with the hammer 13 to generate longitudinal compression waves 70 passing generally along the length of the tree 10 as shown in FIG. 2. The angle θ of the transmitting acoustic probe 12 ensures that energy is directed into a compression wave along the trunk of the tree 10. The angle θ' of receiving acoustic probe 14 in turn provides that the longitudinal compression waves 70 produce an axial force along the spike 28 that may be sensed by a piezoelectric accelerometer 82 as has been described.

When the hammer 13 strikes the impact cap 66, the internal switch provides the acoustic start signal received by infrared receiver 77, causing the initiation of a timer internal to the microcontroller 80.

Figure 5:
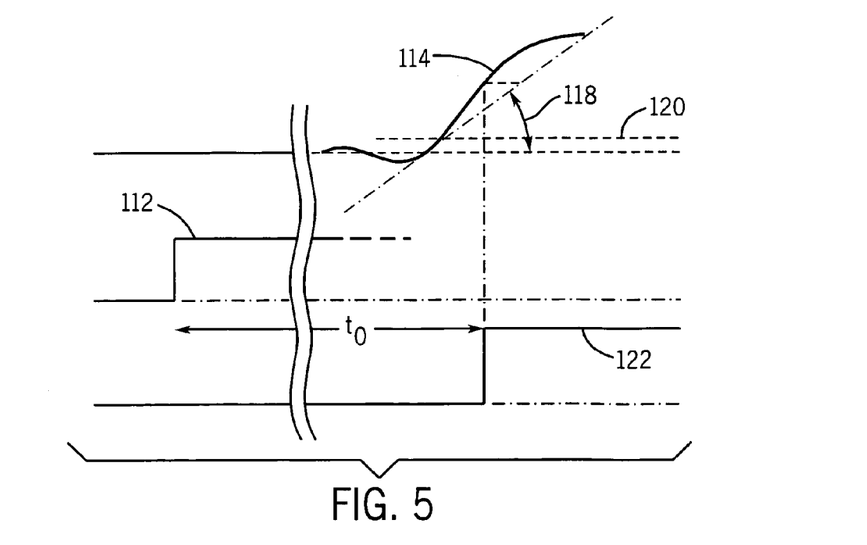
FIG. 5 is a set of three plots indicating from top to bottom, a received acoustic signal, a transmitted acoustic start signal, and an acoustic stop signal derived from the received acoustic signal using an amplitude-independent detection technique.

Referring now to FIG. 5, at a given time after a closure of the switch in impact cap 66 as indicated by an upward transmission of an acoustic start signal 112, the receiving acoustic probe 14 will detect a transmitted compression wave signal 114 through accelerometer 82. This digitized signal may be filtered to reduce high frequency noise unlikely to be a compression wave through wood, and then is analyzed to detect a slope exceeding a predetermined slope 118, the particular value being dependent on the amplification of the signal and the time base of the measurement. The filtering and analyses may be performed through software executed by the microcontroller 80 or by a digital signal processor (DSP) or by discrete components implementing analog filters and slew rate filters as would be understood in the art from this description. If the signal equals or exceeds the slope 118 and is at least of a predetermined threshold 120, then the acoustic pulse is considered properly received and a stop pulse is generated, and a time fixed on the clock as derived from the retrospective analysis of the rising edge of a logical acoustic stop signal 122. The slope sensitive detection system reduces sensitivity of the detection time on the amplitude of the signal such as may vary widely according to how hard the forester 11 strikes the transmitting acoustic probe 12 with the hammer 13, the coupling of the transmitting spike 26 and spike 28 to the sapwood 44 and other factors unrelated to the quality of the tree. Other amplitude-independent detection systems can also be envisioned including those that detect particular waveform shapes or frequency content.

At decision block 108, the receive signal is analyzed as described above and if it is acceptable, this is indicated to the forester 11 by a single beep from the audible transducer 79 and at process block 110, and if the rolling three-hit average is acceptable, the forester removes the transmitting acoustic probe 12 and receiving acoustic probe 14. If the signal is not acceptable in meeting the above slope/amplitude criteria, the forester 11 is instructed via three beeps from the audible transducer 79 to strike the transmitting acoustic probe 12 again at process block 106 until a suitable signal is obtained.

The elapsed time between the start of the acoustic start signal 112 and rising edge of the acoustic stop signal 122, $t_0$, is considered the time required for a pulse to proceed from transmitting acoustic probe 12 to receiving acoustic probe 14. The acoustic wave speed through the tree $C_{tree}$ is determined by the microcontroller 80 using the following equation:

$$C_{tree} = \frac{L_0}{t_0} \qquad (1)$$

where $L_0$ represents the distance determined by the ultrasonic range finder 50 corrected for the displacement of the transmitting acoustic probe 12 and receiving acoustic probe 14 with respect to the housings 18 and 20 as described above.

In a preferred embodiment, to may be modified by subtracting the time of flight in the spikes 26 and 28 between their tips and their respective sensors of switch in impact cap 66 and accelerometer 82 as follows:

$$t_0 = t_m - 2\Delta t \qquad (2)$$

where $\Delta t$ is the time of flight through the steel or other material of the spikes 26 and 28 and $t_m$ is the measured time of flight by the apparatus. The sound speed may be corrected by the measured temperature of the wood.

If the sound speed for a given measurement is within a predefined velocity range, the system provides feedback to the operator by audible or by some other means to eliminate the requirement for the operator to view the PDA screen.

At process block 110, the measure of the quality of the wood is then determined using the sound speed and a number of predictor parameters as arguments to an empirically or theoretically derived function. In the preferred embodiment, the predictor parameters include sound speed as determined above, DBH and the age of the tree, however, tree species, green moisture content, and basic density may also be used. These parameters may be measured for selected trees of a stand or deduced from tree species or other measurements.

In the present preferred embodiment, the function may be implemented in one of the following forms:

$$Y = \alpha X_1^b X_2^c X_3^d \qquad (3)$$

or $$Y = \beta_0 + \beta_1 X_1 + \beta_2 X_2 + \beta_3 X_3 + \beta_{11} X_1^2 + \beta_{22} X_2^2 + \beta_{33} X_3^2 + \beta_{12} X_1 X_2 + \beta_{23} X_2 X_3 + \beta_{13} X_1 X_3 \qquad (4)$$

Y is the wood or fiber property to be predicted;

a, b, c, or the $\beta$ values are experimentally derived constants specific to the equipment and species of the tree; and $X_1$, $X_2$, and $X_3$ are the predictor parameters of $C_{tree}$, DBH and estimated age of the tree.

This data Y may be stored in the PDA 22 and associated with the particular tree which may be marked or identified by location through the use of a GPS device or the like. The information of various trees may be collected to create a "stand summary" providing for stand average values and value ranges for a particular stand of trees. While the forester is collecting data on a plot/stand, when data collected achieve a predefined stand point average, the system provides feedback to the operator by audible or by some other means to eliminate the requirement for the operator to continue any further data collection for that plot/stand.

Figure 7:
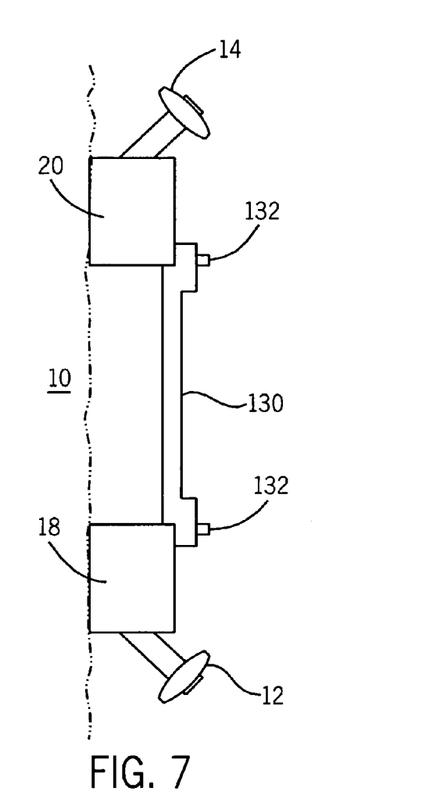
FIG. 7 is a side view of the probes similar to that of FIG. 2 showing the use of a removable separation guide in an alternative embodiment of the invention.

Referring now to FIG. 7, some features of the present invention, for example the pulse detection technique, may be used in an alternative embodiment having a removable separator rod 130 of fixed length which may be fit against each of the housings 18 and 20 on pegs 132 to assist in attaching the transmitting acoustic probe 12, and receiving acoustic probe 14 to the tree 10, and then is removed before measurement.

Although in an ultrasonic range finder 50 is preferred, other distance measuring techniques may be used including those using laser or optical range finders or radio-based range finders may also provide measurement of the separation of the transmitting acoustic probe 12 and the receiving acoustic probe 14. Removable mechanical caliper systems may also be used where the separation is automatically measured by encoders, linear transformers, or the like. Different methods than a hammer strike may be used for generating the excitation signal including an ultrasonic piezoelectric transducer attached to the transmitting acoustic probe 12.

It is specifically intended that the present invention not be limited to the embodiments and illustrations contained herein, but include modified forms of those embodiments including portions of the embodiments and combinations of elements of different embodiments as come within the scope of the following claims.

We claim:

1. An apparatus for testing the wood of trees comprising:
   a) a first and second acoustic probe attachable to a tree at different heights along the trunk to engage wood of the tree and to provide an acoustic transmission signal and an acoustic reception signal indicating, respectively, a time of initiation of an acoustic wave into the wood by the first acoustic probe and a time of receipt of the acoustic wave through the wood at the second probe;
   b) analysis circuitry communicating with the first and second acoustic probes to receive acoustic start and stop signals and to provide a speed of sound measurement of the acoustic wave through the wood; and
   c) a wireless communication link transmitting at least one of the acoustic stop signal and acoustic start signal to the analysis circuitry, the wireless communication link providing a speed of transmission substantially greater than a speed of propagation of the acoustic wave; whereby the first and second acoustic probes may be unencumbered by interconnecting cables.

2. The apparatus of claim 1 wherein the wireless communication link is an infrared diode transmitting the acoustic start signal from the first probe to the analysis circuitry.

3. The apparatus of claim 1 wherein the analysis circuitry is attached to the second acoustic probe.

4. The apparatus of claim 1 further including:
   a data-logging unit storing speed of sound measurements; and
   a second wireless communication link transmitting speed of sound measurement data from the analysis circuitry to the data-logging unit.

5. The apparatus of claim 1 wherein the speed of sound measurement is a velocity of the acoustic wave in wood of the tree.

6. The apparatus of claim 1 wherein the speed of sound measurement is a wood quality value based on a velocity of the acoustic wave in wood of the tree.

7. The apparatus of claim 1 further including a range detecting sensor communicating between the first and second acoustic probes to provide a separation measurement signal indicating a separation between the first and second acoustic probes without substantial acoustic coupling between the first and second acoustic probes other than that provided by the wood; and wherein the analysis circuitry uses the separation measurement signal in determining the speed of sound measurement.

8. The apparatus of claim 1 further including an alignment sensor communicating between the first and second acoustic probes to indicate whether spikes of the first and second acoustic probes lie within a single common plane, wherein the alignment sensor operates without substantial acoustic coupling between the first and second acoustic probes other than that provided by the wood.

9. The apparatus of claim 1 further wherein the second probe further includes a transducer for generating an electrical signal measuring the acoustic wave received at the second probe and including:
a pulse discrimination circuitry receiving the electrical signal and generating a pulse stop signal using an amplitude independent detection process.

10. An apparatus for testing the wood of trees comprising:
a) a first and second acoustic probe attached to the tree at different heights to engage wood of the tree and to provide an acoustic transmission signal and an acoustic reception signal indicating, respectively, a time of initiation of an acoustic signal into the wood by the first acoustic probe and a time of receipt of the acoustic signal through the wood at the second probe;
b) a range-detecting sensor communicating with the first and second acoustic probe to provide a separation measurement signal indicating a separation between the first and second acoustic probes without substantial acoustic coupling between the first and second acoustic probes other than that provided by the wood; and
c) analysis circuitry receiving acoustic signal start and stop signals from the first and second acoustic probes and the separation measurement signal from the range detecting sensors to provide a speed of sound measurement through the wood.

11. The apparatus of claim 10 wherein the range-detecting sensor is selected from the group consisting of optical sensors, acoustic sensors, removable mechanical sensors, and radio sensors.

12. The apparatus of claim 10 wherein the range sensor does not provide substantial vibratory coupling between the first and second acoustic probe other than that provided by the wood.

13. The apparatus of claim 10 wherein the first and second probes include spikes adapted to be driven through bark and cambium of the tree to engage a sapwood beneath the cambium.

14. An apparatus for testing the wood of trees comprising:
a) a first and second acoustic probe having spikes that may be driven into a tree at different heights to engage wood of the tree angled along a longitudinal direction to provide an acoustic transmission signal and an acoustic reception signal indicating, respectively, a time of initiation of an acoustic signal into the wood by the first acoustic probe and a time of receipt of the acoustic signal through the wood at the second probe;
b) an alignment sensor communicating between the first and second acoustic probes to indicate whether the spike of the first and second acoustic probes lies within a single common plane; and
c) analysis circuitry receiving acoustic signal start and stop signals from the first and second acoustic probes to provide a speed of sound measurement through the wood.

15. The apparatus of claim 14 wherein the first and second acoustic probes include housings that have guide projections that lie in a substantially horizontal plane when the spikes are properly angled within the wood.

16. The apparatus of claim 14 wherein at least one spike includes a radially extending handle to assist in alignment of the spike.

17. The apparatus of claim 14 wherein at least one spike is removably attached to the acoustic probe to be driven into the wood and then attached to a remainder of the acoustic probe.

18. The apparatus of claim 14 wherein the analysis circuitry provides a signal to the user indicating the measurement is acceptable.

19. An apparatus for testing wood of trees comprising:
a) a first acoustic probe attachable to the tree at a first height to engage the wood and to provide an acoustic pulse into the wood of the tree and an electrical pulse start signal wirelessly communicated to a second acoustic probe;
b) the second acoustic probe attachable to the tree at a second height to engage the wood of the tree and to provide an electrical signal measuring the acoustic pulse at the second acoustic probe;
c) pulse discrimination circuitry receiving the electrical signal and generating a pulse stop signal using an amplitude-independent detection process; and
d) analysis circuitry receiving pulse start and stop signals from the first and second acoustic probes to provide a speed of sound measurement through the wood.

20. The apparatus of claim 19 wherein the pulse start signal is provided by an electrical switch actuatable by a striking of the first acoustic probe with a mallet.

21. The apparatus of claim 19 wherein the pulse discrimination circuitry detects a slope of the electrical signal and produces the pulse stop signal when the slope exceeds a predetermined value.

22. A method for testing wood of trees comprising the steps of:
a) measuring a sound speed of an acoustic wave through the wood from a first probe to a second probe that is not physically tethered to the first probe, the first and second probes being affixed to the tree;
b) measuring a diameter of the tree at a predetermined height; and
c) providing the sound speed and tree diameter as arguments to an empirically derived model providing an indication of wood quality.

23. The method of claim 22 further including the step of measuring ambient air temperature and providing ambient air temperature as an argument to the empirically derived model.

24. The method of claim 22 further including the step of measuring wood temperature and providing wood temperature as an argument to the empirically derived model.

25. The method of claim 22 further including the step of determining wood species and providing wood species as an argument to the empirically derived model.

26. The method of claim 22 further including the step of estimating tree age and providing tree age as an argument to the empirically derived model.

27. The method of claim 22 further including the step of determining or estimating tree moisture content and providing tree moisture content as an argument to the empirically derived model.

28. The method of claim 22 further including the step of determining tree density and providing tree density as an argument to the empirically derived model.

* * * * *